(12) United States Patent
Lou et al.

(10) Patent No.: US 9,374,867 B2
(45) Date of Patent: Jun. 21, 2016

(54) ILLUMINATION APPARATUS AND METHOD

(75) Inventors: Di Lou, Shanghai (CN); Sheng Peng, Shanghai (CN); Jinfeng Huang, Eindhoven (NL); Tony Petrus Van Endert, Lommel (BE)

(73) Assignee: Koninklijkle Philips Electronics N.V., Eindhoven (NL)

( * ) Notice: Subject to any disclaimer, the term of this patent is extended or adjusted under 35 U.S.C. 154(b) by 105 days.

(21) Appl. No.: 13/977,178

(22) PCT Filed: Dec. 27, 2011

(86) PCT No.: PCT/IB2011/055966
§ 371 (c)(1),
(2), (4) Date: Jun. 28, 2013

(87) PCT Pub. No.: WO2012/090154
PCT Pub. Date: Jul. 5, 2012

(65) Prior Publication Data
US 2013/0278150 A1    Oct. 24, 2013

(30) Foreign Application Priority Data

Dec. 31, 2010   (WO) ................ PCT/CN2010/002224

(51) Int. Cl.
*H05B 37/02*    (2006.01)

(52) U.S. Cl.
CPC ............ *H05B 37/02* (2013.01); *H05B 37/0227* (2013.01)

(58) Field of Classification Search
CPC .............. G08B 5/00; G08B 5/36; G08B 7/00; H05B 37/02; H05B 37/029; H05B 37/0272; H05B 37/0218
USPC ........ 315/152, 155, 158; 340/815.65, 815.66, 340/815.68
See application file for complete search history.

(56) References Cited

U.S. PATENT DOCUMENTS 7,564,368 B2 *   7/2009  Segall ........................ 340/815.4
2009/0273287 A1   11/2009  Segall

FOREIGN PATENT DOCUMENTS

| CN | 2070863 U | 2/1991 |
|---|---|---|
| CN | 2496037 Y | 6/2002 |
| CN | 2596184 Y | 12/2003 |
| CN | 2847005 Y | 12/2006 |
| CN | 200946769 Y | 9/2007 |
| CN | 2010021794 Y | 2/2008 |
| CN | 101285556 A | 10/2008 |
| CN | 201462647 U | 5/2010 |
| CN | 201475774 U | 5/2010 |
| CN | 101725860 A | 6/2010 |
| CN | 201513785 U | 6/2010 |
| WO | 2004049767 A1 | 6/2004 |

* cited by examiner

*Primary Examiner* — John Poos

(57) ABSTRACT

The application discloses an illumination apparatus comprising: a light source configured to generate light; a detector configured to detect the posture of an object within a time period and generate a plurality of signals corresponding to this time period; and a processor configured to determine the status of the object within the time period, based on the plurality of signals, and adjust the light source to generate light corresponding to the determined status of the object.

13 Claims, 6 Drawing Sheets

(a)

(b)

ILLUMINATION APPARATUS AND METHOD

FIELD OF THE INVENTION

The present invention relates to the field of lighting, in particular consumer luminaires.

BACKGROUND OF THE INVENTION

Illumination apparatus, e.g., desk lamps, floor lamps, wall lamps, are widely used by people when reading or working One major concern when using these illumination apparatus relates to the user's posture.

A desk lamp using ultrasonic sensors to detect a user's posture is disclosed in Chinese utility model CN2847008Y. The desk lamp comprises a head-detection circuit and a body-detection circuit, both equipped with an ultrasonic sensor capable of transmitting and receiving ultrasonic signals. The body-detection circuit is used to detect whether the user is sitting in front of the desk, and the head-detection circuit is used to detect whether the head of the user is below a preset horizontal plane. If the latter is the case, the head is below a preset alarm plane, meaning that the head cannot reflect the ultrasonic waves sent from the head-detection circuit back to the head-detection circuit, which will result in an alarm from an alarm circuit to remind the user to raise his/her head to get the right sitting posture. The proposed desk lamp is based on the assumption that a lower height of the head is equivalent to an improper sitting posture, and has the disadvantage that it generates a noticeable alarm signal which is probably disturbing to the user when he is working and which highly relies on the user's conscious response to the alarm signal.

There is always a need to correct people's posture when they are reading or working.

SUMMARY OF THE INVENTION

One object of the present invention is to detect the posture of people when they are reading or working, and to utilize the adjustment of lighting conditions to help people adjust their posture, particularly by means of a method which is less noticeable, or even perceived as inconspicuous by the people concerned.

According to one embodiment, an illumination apparatus is provided. The illumination apparatus comprises a light source configured to generate light; a detector configured to detect the posture of an object within a time period and generate a plurality of signals corresponding to this time period; and a processor configured to determine the status of the object within the time period, based on the plurality of signals, and adjust the light source to generate light corresponding to the determined status of the object.

The basic idea is to detect the posture of a user of the illumination apparatus within a preset time period and collect a plurality of signals, each signal representing one corresponding detected posture, and then analyze these signals to determine the user's status within the preset time period. It is to be noted that the term "posture" in the present invention focuses more on a user's body posture within a relatively short time period, or even a time instant, for example a temporal posture, or an instant posture, or a posture within a quite short time period compared to the relatively longer preset time period for determining the "status" of the body of the user. For example, the "posture" can be an instant posture when the detector performs the detection. The term "status" in the present invention is more focused on the user's status within the preset time period, for example, a statistical status or posture within the preset time period, or a status or posture that is most frequently assumed within the preset period, or a representative posture for representing the user's sitting posture within the preset time period. For example, the "status" can be a natural sitting well posture, a forward bending sitting posture, a well-concentrated sitting posture, which means the movement of the body of the user within the preset time period is normal, a poor concentration sitting posture, which means the user has more body movement within the preset time period, and an overly concentrated sitting posture, which means the user has less body movement within the preset time period. The term "movement" in the present invention can refer to the number of body movements in the preset time period, or the extend of the body movement in space within the preset time period, or a combination thereof, or to any other applicable metrics used to measure people's body movement.

After the status of the user has been determined, the present invention can advantageously be used to help people adjust their postures by utilizing the adjustment of the light. More advantageously, the adjustment of the light, making the user adjust his/her posture, is perceivable by the user, however, it is less noticeable or at least in a less interruptive way.

Optionally, in one embodiment, the detector comprises a plurality of ultrasonic sensors, and each sensor is capable of transmitting ultrasonic signals and/or receiving reverberative ultrasonic signals. In some embodiments, each sensor can only receive the ultrasonic signals sent by it and reflected by the user. In some further embodiments, each sensor can receive the mixture of ultrasonic signals sent by other sensors and by itself and reflected by the user. Also, in some embodiments, some ultrasonic sensors only perform the task of transmitting ultrasonic signals, while other ultrasonic sensors perform the task of receiving reverberative ultrasonic signals. The capability of processing these reverberative ultrasonic signals can reside in the sensors themselves, or in a separate processor packaged into the detector, or even in a standalone processor physically arranged outside the detector, or even can be integrated into the term "processor" of claim 1, or may be achieved in any other applicable form. For the purpose of easy-description only, hereinafter the capability of processing these reverberative ultrasonic signals and converting them into the detected postures is incorporated into the detector by way of example. Those skilled in the art should understand that this function can reside in different modules, devices, locations, and may assume different forms. Irrespective of the variants used, they will still fall within the protective scope of the present invention.

In one embodiment, the illumination apparatus can measure whether the user is sitting straight, or leaning forward, or leaning backward. The detector comprises a plurality of ultrasonic sensors, a first portion of the sensors being configured to measure a first distance between a first part of the user, for example, the head, and the illumination apparatus, for example, a desk lamp, a second portion of the sensors being configured to measure a second distance between a second part of the user, for example, the chest, and the illumination apparatus, for example, a desk lamp. Knowing the first and the second distance, the processor can calculate the angle of bend of the user, and compare it with a preset angle parameter, e.g., 25~30 degrees. When the angle of bend measured from the vertical plane exceeds the preset angle parameter, the processor can adjust the light source, for example by sending a signal to the light source, to increase the light intensity or the CCT (Correlated Color Temperature) of the light or both. An increase of the light intensity or CCT can make the user perceive the increase of the light intensity and urge him/her to more or less adjust his/her posture backward, advantageously, in an unconscious way. Therefore, the advantage of adjusting the posture without, or only to a limited extent, interrupting the user's current activities is reached. In this embodiment, the term "distance" can be a statistical spatial distance obtained from a plurality of instant spatial distances measured within the preset time period. For the purpose of easy description, the term "distance" is intended to represent the direct spatial distance between the body or a part of the body of the user and the illumination apparatus, but it should be understood by the person skilled in the art that the term "distance" also can mean the distance between the body or a part of the body of the user and a reading area or reading material, e.g., a book or screen. Considering the triangular positional relationship between the user, a desk lamp, and a book/screen, and the relatively stable distance between the desk lamp and the book/screen and the relatively minor change of the angle between the virtual line connecting the desk lamp and the book/screen and the virtual line connecting the desk lamp and the user, the relationship between the "spatial distance" between the user and the book/screen and the "distance" between the desk lamp and the user can be calculated. Thus, the optimal spatial distance between the user and the book/screen can be converted to and represented by the distance between the illumination apparatus and the user.

In another embodiment of the present invention, the distance between the illumination apparatus and the user can be measured, and if the measured distance exceeds a preset distance parameter, the processor can adjust the light source to increase the light intensity and/or the CCT of the light.

The level of concentration of a user on his/her work/reading is always a metric to measure whether people focus on their work or not. Over-concentration may cause people's muscles to become tensioned for a prolonged time period, and poor concentration may impact people's working efficiency. In one embodiment of the present invention, the processor is further configured to analyze the plurality of signals to determine the movement frequency of the user, and compare the determined movement frequency with a first preset frequency parameter to determine the status of the object, and when the determined movement frequency is lower than the first preset frequency parameter, the processor is further configured to adjust the light source to decrease the CCT of the light or increase the yellowish component of the light. A warmer white light with a lower CCT or a light containing more of a yellowish component makes people less concentrated and more relaxed. By adjusting the light, the concentration level of the user can be decreased.

In a further embodiment, after the decrease of the CCT or the increase of the yellowish component of the light, the detector may further detect the postures of the user within a subsequent second time period, as a result of which a second plurality of signals are obtained. Furthermore, a second movement frequency can be determined from the second plurality of signals. When the second movement frequency is higher than the first preset frequency parameter, the processor can notify the light source to increase the CCT of the light or lower the yellowish component of the light. Consequently, the concentration level of the user will not decrease any more.

In these two embodiments, the first preset frequency parameter is the threshold to judge whether the user is over-concentrated or well-concentrated.

In another embodiment, the processor is further configured to analyze the plurality of signals to determine the movement frequency of the object, and compare the determined movement frequency with a second preset frequency parameter to determine the status of the object, and when the determined movement frequency is higher than the second preset frequency parameter, the processor is further configured to adjust the light source to increase the CCT of the light or increase the bluish component of the light. Cooler white light with a higher CCT or light containing more of a bluish component can increase people's concentration level and alertness level.

In a further embodiment, after the decrease of the CCT or the increase of the yellowish component of the light, the detector may further detect the postures of the user within a subsequent, second time period, and consequently a second plurality of signals is obtained. Furthermore, a second movement frequency can be determined from the second plurality of signals. When the second movement frequency is lower than the second preset frequency parameter, the processor can notify the light source to decrease the CCT of the light or lower the bluish component of the light. Consequently, the concentration level of the user will not increase any more.

In these two embodiments, the second preset frequency parameter is the threshold to judge whether the user is poorly concentrated or well-concentrated.

The first and the second preset frequency parameters can be set based on people's preference, people's habit, and/or the posture detection sampling rate. The person skilled in the art also should understand that other applicable metrics capable of measuring people's concentration also can be used in the apparatus and methods of the present invention.

The person skilled in the art should understand that the term "movement" in the present invention can refer to the number of body movements in the preset period, or to the extent of the body movement in space in the preset period, or a combination thereof, or to any other applicable metrics used to measure people's body movement.

For measuring the movement of the body of the user, especially the distance between the user and the illumination apparatus, two or more ultrasonic sensors can be used. With the change of the measured distance, indicated by numbers above and below a preset distance parameter or by numbers larger than a preset maximum distance parameter, the movement frequency and the second movement frequency can be determined.

Normally, two vertically arranged ultrasonic sensors are enough to measure the distance between the user and the illumination apparatus. In one embodiment, for measuring the movement in the left-and-right direction, not only in the direction of fore-and-aft, two more horizontally arranged ultrasonic sensors can be provided. The sensors can be placed at the pole of the illumination apparatus, or at the shade or any other suitable place.

According to one embodiment of the present invention, there is provided a method of providing illumination. The method comprises the steps of a) detecting the posture of an object within a time period and generating a plurality of signals corresponding to the time period; b) determining the status of the object within the time period, based on the plurality of signals; and c) generating light corresponding to the determined status of the object.

Furthermore, a set of computer executable instructions, capable of performing the methods proposed in the present invention, is also provided. While the invention has been discussed in the context of computer executable instructions, it should be understood that the instructions may be implemented in hardware circuitry, computer program code, or any combination of hardware circuitry and computer program code.

These and other aspects of the invention will be apparent from and elucidated with reference to the embodiments described hereinafter.

BRIEF DESCRIPTION OF THE DRAWINGS

The proposed illumination apparatus will be described hereinbelow by means of exemplary embodiments and with reference to the accompanying drawings, without the scope of protection given by the patent claims being limited.

In the drawings.

DETAILED EMBODIMENTS OF THE INVENTION

Figure 1:
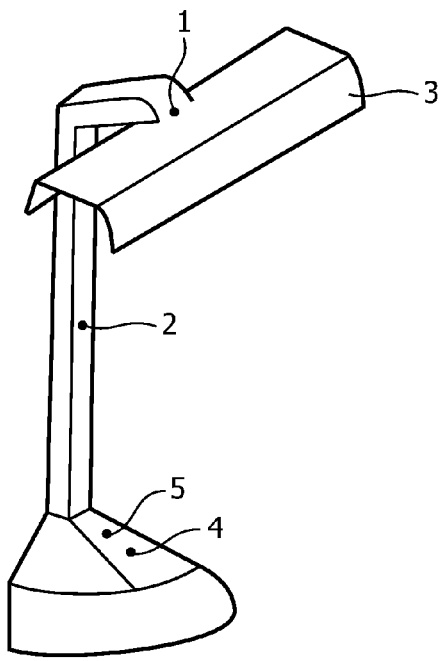
FIG. 1 is a diagrammatic view of a known desk lamp in accordance with the state of the art.

While the invention covers various modifications and alternative constructions, embodiments of the invention are shown in the drawings and will hereinafter be described in detail. However, it should be understood that the specific description and drawings are not intended to limit the invention to the specific forms disclosed. On the contrary, the scope of the claimed invention is intended to include all modifications and alternative constructions thereof falling within the scope of the invention as expressed in the appended claims.

Figure 2:
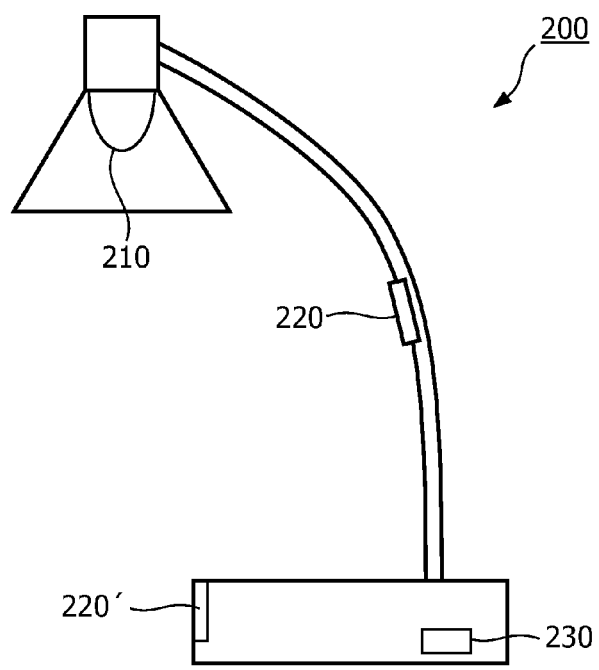
FIG. 2 diagrammatically shows an example of an embodiment of the proposed illumination apparatus.

FIG. 2 illustrates an exemplary desk lamp 200 according to one embodiment of the present invention. The desk lamp 200 comprises a light source 210, a detector 220 and a processor 230. The light source 210 is used to generate light to illuminate a target object or a target area. The detector 220 is used for detecting the posture of an object within a time period and for generating a plurality of signals corresponding to the time period. The processor is used for determining the status of the object within the time period, based on the plurality of signals, and for adjusting the light source accordingly to generate light corresponding to the determined status of the object. The locations of these three elements are given by way of example only; they can be placed at different locations, depending on practical design and needs. For example, the detector 220' can be placed at the base of the desk lamp, or the detector can comprise multiple parts, the first part 220 being placed at the pole of the desk lamp, and the second part 220' being placed at the base of the desk lamp.

In one embodiment, the detector 220/220' comprises a plurality of ultrasonic sensors. Each ultrasonic sensor can transmit ultrasonic signals in a continuous way, or in a periodic or non-periodic way, and receive the reverberative ultrasonic signals reflected by the user. An ultrasonic sensor may only receive or recognize the reverberative ultrasonic signals comprising solely the ultrasonic signal component transmitted by itself, or may also receive or recognize the reverberative ultrasonic signals comprising the ultrasonic signal components transmitted by other ultrasonic sensors. The operation of transmitting the ultrasonic signals and/or receiving the reverberative ultrasonic signals and/or processing the received reverberative ultrasonic signals so as to obtain the postures of the users, can be performed by each sensor independently, or by at least part of the sensors collectively. A person skilled in the art should understand that the ultrasonic sensors for detecting the postures of the user are given by way of example only and that other applicable sensors capable of detecting the posture of the user or the distance between two objects are also applicable for the present invention and within the scope of the invention.

The plurality of sensors 220/220' can be centralized at one location of the illumination apparatus 200; it is also practical to distribute the plurality of sensors at different locations of the illumination apparatus. Accordingly, the algorithms of the sensors for processing the reverberative signals can be different, based on the different arrangement of the sensors.

Hereinafter, the working principle of the illumination apparatus proposed in the present invention is described in some embodiments in the form of methods.

Figure 3:
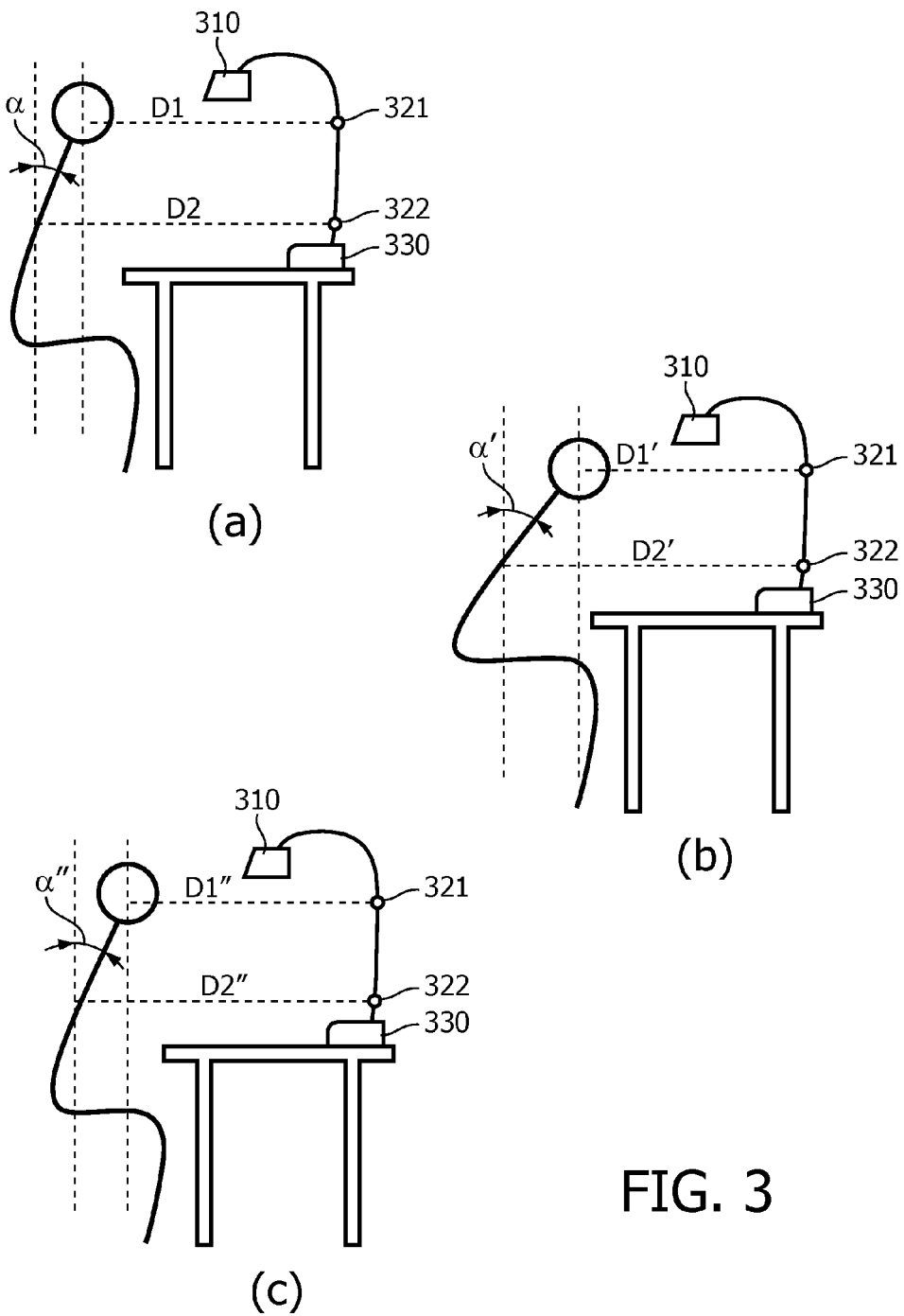
FIG. 3 depicts the adjustment of the postures of the user according to some embodiments.

In FIG. 3, there are two distributed ultrasonic sensors 321 and 322 placed at a different location in the illumination apparatus. For example, the sensor 321 is for measuring the first distance D1 between the head of the user and the sensor 321, and the sensor 322 is for measuring the second distance D2 between the chest of the user and the sensor 322. The terms "head" and "chest" represent two different parts of the user; other applicable parts of the user also can be used as measuring objects in practice. The two distances D1 and D2 can be two respective groups comprising a plurality of instant distances measured by the two sensors 321 and 322 at the sampling duration; they also can be two individual distances, each representing a statistical or average distance calculated from a corresponding group of instant distances measured by the corresponding sensor 321 or 322. The calculation operation can be performed in the detector, or in the processor 330. For the purpose of easy-description only, the two distances D1 and D2 represent the statistical distances in the embodiments illustrated in FIG. 3. The processor 330 can calculate an angle of bend α of the body of the user relative to the vertical plane, based on the two distances D1 and D2. Then the processor 330 compares the angle of bend α with a preset angle parameter β, which is regarded to represent a good sitting posture, for example a straight sitting posture which includes an angle of 25~30 degrees with the vertical plane. In FIG. 3A.a, the calculated angle of bend α is smaller than the preset angle parameter β; consequently, there is no need for the processor to adjust the light source 310. In the next period, measurements show that the angle of bend α is already larger than the preset angle parameter β; consequently, the processor 330 sends a signal to the light source 310 to increase the light intensity, or the CCT, or both. Perceiving the increase of the light intensity and/or CCT, may urge the user to sit backward, so that the sitting posture is adjusted. Optionally, if in the subsequent period the angle of bend α is smaller than the preset angle parameter β again, the processor 330 can instruct the light source 310 to decrease the light intensity or the CCT or both, which will prevent the user from sitting backward too much.

Figure 4:
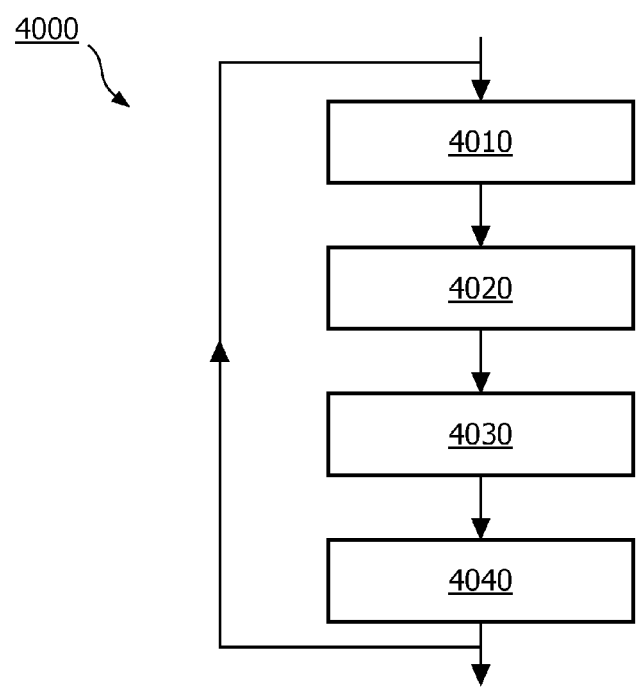
FIG. 4 depicts the work flow chart of some methods according to some embodiments.

FIG. 4 illustrates a flow chart of a method corresponding to the embodiments shown in FIG. 3. In the method 4000, step 4010 measures the first distance D1, and step 4020 measures the second distance D2. After that, step 4030 calculates the angle of bend α based on the two distances D1 and D2, and compares the angle of bend α with the preset angle parameter β. Accordingly, step 4040 decides whether or not to adjust the light intensity and/or the CCT, based on the comparison result of step 4030. The operation of step 4040 can be to increase or decrease the light intensity and/or the CCT, depending on the comparison between α and β.

Instead of calculating the angle of bend by utilizing two individual sensors or two sets of sensors, according to an embodiment of the present invention, it is also practical to utilize one individual sensor or one centralized set of sensors to adjust the user's posture, e.g., adjust the distance between the user and the illumination apparatus. As shown in another embodiment shown in FIG. 3A, only one sensor 321 or one set of sensors 321 is incorporated in the illumination apparatus; therefore only one distance D1 is available. The measured distance D1 can be compared with a preset distance parameter γ. When the measured distance D1 is larger than the preset distance parameter γ, there is no need for the processor 330 to adjust the light source 310. When the measured distance D1 is smaller than the preset distance parameter γ, the processor 330 can signal the light source 310 to increase the light intensity and/or (?) the CCT of the light. After perceiving the increase of the light intensity and/or the CCT, the user may feel urged to sit backward due to the physiological effect. This physiological effect normally is hard to notice by a human being, and therefore the adjustment of the posture is not interruptive, or at least less interruptive, to the user's current activities.

The level of concentration is a metric that can be used to measure the degree to which people focus on their work. However, over-concentration for a relatively long time period may cause people's muscles to become tensioned and will further make people feel tired, while poor concentration may impact people's working efficiency.

Figure 5:
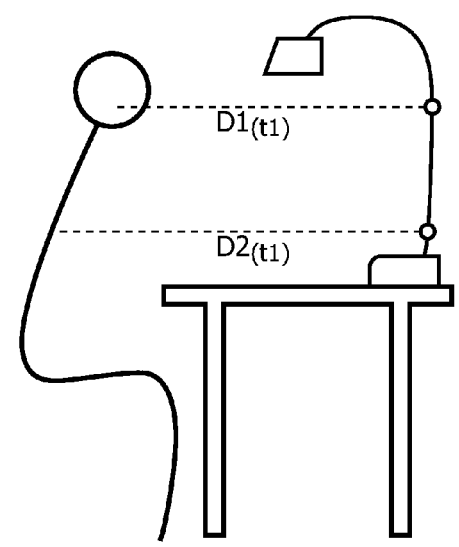
FIG. 5 depicts the adjustment of the postures of the user according to some embodiments.
Figure 5:
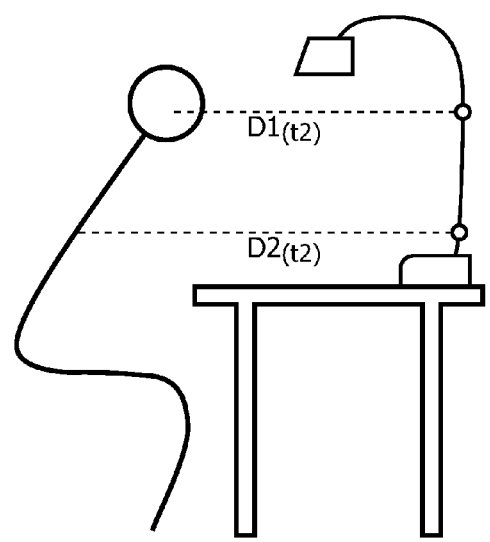

In an embodiment shown in FIG. 5, the movement frequency of the body of the user is measured, which can be used to obtain the level of concentration of the user. In FIG. 5(a), a group of instant distances $D1(t_i)$ are measured. $D1(t_i)$ represents an instant distance between the head of the user and the illumination apparatus, wherein $t_i$ represents the instant at which the detector detects the posture of the user. From the group of instant distances $D1(t_i)$, the processor can calculate the movement frequency of the head of the user. The processing algorithm can be varied. For example, the processor can calculate the difference between two consecutive instant distances $t_j$ and $t_{j+1}$. When the difference exceeds a preset distance change parameter, e.g., 5 cm, the movement frequency count can be increased by one. When the movement frequency within the preset period is lower than a first preset frequency parameter, it is reasonable to conclude that the user is over-concentrated. Consequently, the process can control the light source to decrease the CCT of light or increase the yellowish light component, or both. Warmer light with a higher CCT or light with a higher yellowish spectral component can make people less concentrated and more relaxed. Of course, another sensor can be used to measure another distance, for example D2, representing the distance between the chest of the user and the illumination apparatus. While the movements of more parts of the body are measured, the accuracy with which the user's level of concentration is obtained is higher.

In a further embodiment, the postures of the user in several consecutive time periods are measured. If, in the first time period, it is found that the user is in an over-concentrated status, the CCT of the light is decreased and/or the yellowish component of the light is increased. Subsequently, the postures of the user in the second period are measured, and a new second movement frequency corresponding to the second period is obtained. If the user is still found to be in an over-concentrated status, the CCT can be continuously decreased and/or the yellowish component can be continuously increased, until a preset threshold has been reached. If the second movement frequency is larger than the first preset frequency parameter, which means the user is not in an over-concentrated status, there is no need to decrease the CCT or increase the yellowish component. Optionally, the CCT of the light can be increased, and/or the yellowish component of the light can be decreased, until an applicable value has been reached. By using this method, the level of concentration of the user and the change of the level of concentration can be continuously monitored, so that the user can be kept in a good working status.

In another embodiment shown in FIG. 5, poor concentration of the user can be detected and corrected by adjusting the light accordingly. When a plurality of signals is obtained after detecting the postures of the users within a preset time period, the processor can analyze them to determine the movement frequency of the user, and compare it with a second preset frequency parameter. When the movement frequency exceeds the second preset frequency parameter, it can be concluded that the user is in a poor-concentration status. Accordingly, the processor can notify the light source to increase the CCT of the light and/or increase the bluish component of the light. Cooler light with a lower CCT and light containing more of a bluish spectral component can increase people's concentration and alertness level.

Similar to the embodiment of continuously monitoring the level of concentration after it has been detected that the user is in an over-concentrated status, in a further embodiment, the level of concentration of the user also can be continuously monitored after it has been detected that the user is in a poor-concentration status. Similarly, a second movement frequency is obtained for the next consecutive period. If the second movement frequency is lower than the second preset frequency parameter, the CCT of the light and/or the bluish spectral component of the light can be decreased in order to avoid that the people change from a poor-concentration status to an over-concentrated status.

Figure 6:
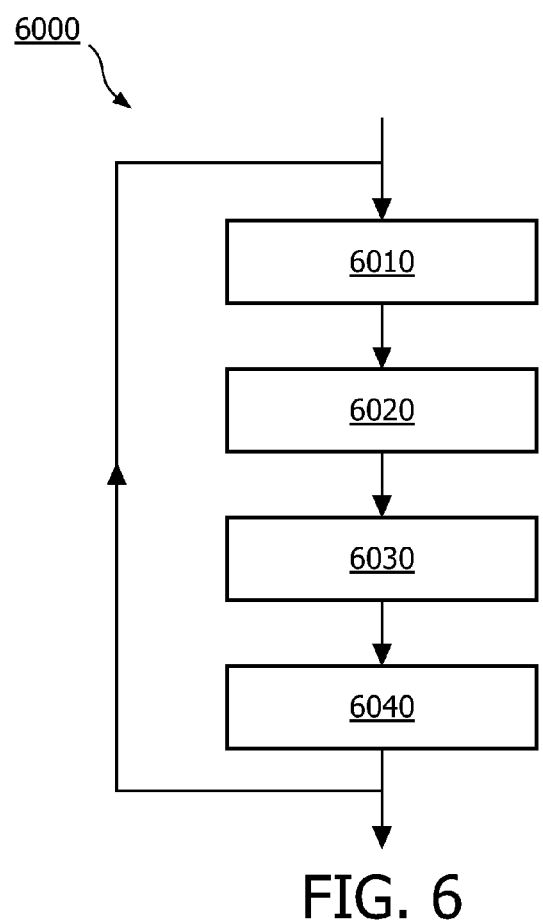
FIG. 6 depicts the work flow chart of some methods according to some embodiments.

FIG. 6 depicts the flow chart of the methods used in the embodiments illustrated by FIG. 5. In the method 6000, step 6010 first detects the postures of the user within a time period, and a plurality of signals is obtained. In step 6020, the movement frequency of the user is calculated on the basis of the plurality of signals obtained in step 6010. In step 6030, the movement frequency is compared with a preset frequency parameter, which can be the first and/or the second preset frequency parameter, so as to determine the level of concentration of the user in the current time period. Subsequently, the light is adjusted by changing the CCT and/or the yellowish component and/or the bluish component, in step 6040. From the flow chart it is clear that the four steps 6010, 6020, 6030 and 6040 can be executed recurrently, so that the concentration level of the user can be continuously monitored and adjusted accordingly.

Although the present invention is described with reference to the embodiment shown in the drawings, it should be understood that the present invention may be embodied in many alternative forms including any combination of hardware and software. In addition, any suitable size, shape or type of materials, elements, computer program elements, computer program code, or computer program modules could be used.

Below, a computer program segment written in a computer primitive programming language is given by way of example:

```
Switch (Detection result)
{
        Case leaving: switch off the light; status = off; break;
        Case leaning forward too much:
                Sending signals to the light source to increase light intensity
                and/ or CCT; break;
        Case overly-concentrated:
                Sending signals to the light source to decrease light CCT
                and/or increase yellowish spectral component of the light; break;
        Case well-concentrated:
                break;
        Case poorly-concentrated:
                Sending signals to the light source to increase CCT and/or
                increase bluish spectral component of the light; break;
        Case unknown:
                break;
}
```

Figure 7:
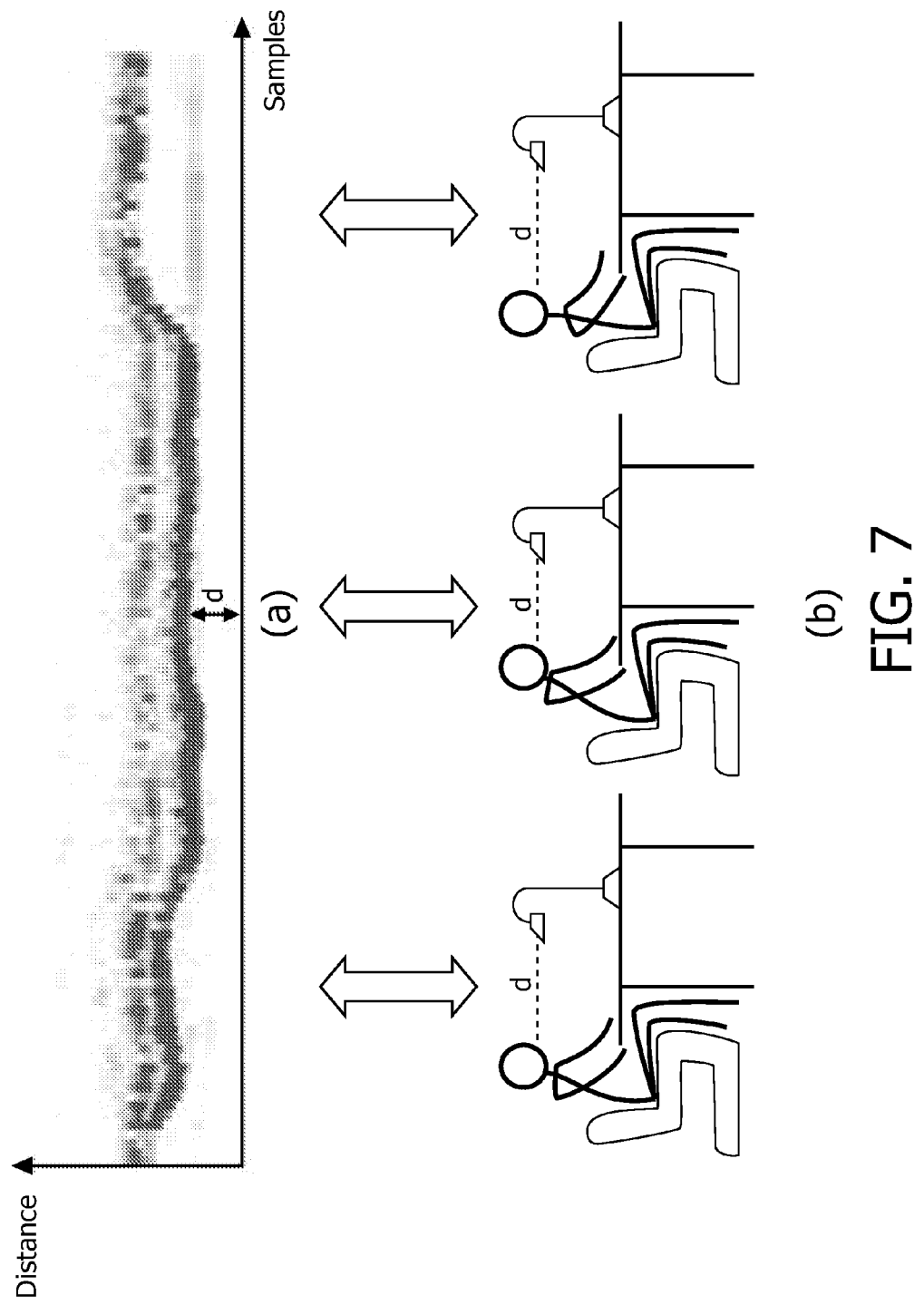
FIG. 7 gives the experiment data and the adjustment of the posture of the users by utilizing the illumination apparatus and methods of the present invention.

FIG. 7 gives some experiment data and adjustments of the posture of users obtained from the application of the proposed illumination apparatus and methods by the inventors in experiments. From left to right, FIG. 7.b depicts the change of the posture and FIG. 7.a illustrates the measured distance between the user and the illumination apparatus. The rightmost drawing in FIG. 7.b is the result of some of the embodiments of the present invention being used to adjust the posture of the user.

Some or all of the steps of the methods as described above may alternatively be implemented by a processor in combination with e.g. a computer program. The computer program comprises computer readable code which, when run on the processor, enables at least some steps of any one of the methods described herein to be performed. The computer program may be stored on a computer-readable medium.

While the invention has been illustrated and described in detail in the drawings and foregoing description, such illustration and description are to be considered illustrative or exemplary and not restrictive. The invention is not limited to the disclosed embodiments. The different embodiments described above and in the claims can also be combined. Other variations to the disclosed embodiments can be understood and effected by those skilled in the art in practicing the claimed invention, from the study of the drawings, the disclosure and the appended claims.

In the claims, the word "comprising" does not exclude other elements or steps, and the indefinite article "a" or "an" does not exclude a plurality. The mere fact that measures are recited in mutually different dependent claims does not indicate that a combination of these measures cannot be used to advantage. The reference signs in the claims should not be construed as limiting the scope of these claims.

The invention claimed is:

1. An illumination apparatus for reading or working comprising:
   a light source configured to generate light;
   a detector configured to detect postures of a user within a time period and generate a plurality of signals corresponding to the time period;
   a processor configured to determine the status of the user within the time period, based on the plurality of signals, and adjust the light source to generate light corresponding to the determined status of the user to adjust posture of the user or a concentration level of the user; and
   wherein a first portion of the plurality of ultrasonic sensors and a second portion of the plurality of ultrasonic sensors are configured to respectively measure a first distance between a first part of the object and the illumination apparatus and a second distance between a second part of the object and the illumination apparatus, and the processor is further configured to process the plurality of signals to determine an angle of bend of the object and compare the angle of bend with a preset angle parameter, and, when the angle of bend is larger than the preset angle parameter, adjust the light source to increase at least one of the light intensity or the CCT of the light.

2. The illumination apparatus of claim 1, wherein the detector comprises a plurality of ultrasonic sensors, each ultrasonic sensor being capable of transmitting ultrasonic signals and/or receiving reverberative ultrasonic signals.

3. The illumination apparatus of claim 1, wherein the processor is further configured to process a second plurality of signals collected within a subsequent second time period, and when a second angle of bend determined based on the second plurality of signals is smaller than the preset angle parameter, the processor is further configured to adjust the light source to decrease at least one of the light intensity or the CCT of the light.

4. The illumination apparatus of claim 1, wherein the processor is further configured to compare the plurality of signals with a preset distance parameter to determine whether a distance between the user and the illumination apparatus is smaller than the preset distance parameter, and, when the distance between the user and the illumination apparatus is determined to be smaller than the preset distance parameter, the processor is further configured to adjust the light source to increase at least one of the light intensity or the CCT of the light.

5. The illumination apparatus of claim 1, wherein the processor is further configured to analyze the plurality of signals to determine a movement frequency of the user, and compare the determined movement frequency with a first preset frequency parameter to determine the status of the user, and when the determined movement frequency is smaller than the first preset frequency parameter, the processor is further configured to adjust the light source to decrease the CCT of the light or increase the yellowish component of the light.

6. The illumination apparatus of claim 5, wherein the processor is further configured to analyze a second plurality of signals collected within a subsequent second time period to determine a second movement frequency of the user, and when the determined second movement frequency is higher than the first preset frequency parameter, the processor is further configured to adjust the light source to increase the CCT of the light or decrease the yellowish component of the light.

7. The illumination apparatus of claim 1, wherein the processor is further configured to analyze the plurality of signals to determine a movement frequency of the user, and compare the determined movement frequency with a second preset frequency parameter to determine the status of the user, and when the determined movement frequency is higher than the second preset frequency parameter, the processor is further configured to adjust the light source to increase the CCT of the light or increase the bluish component of the light.

8. The illumination apparatus of claim 7, wherein the processor is further configured to analyze a second plurality of signals collected within a subsequent second time period to determine a second movement frequency of the user, and when the determined second movement frequency is lower than the second preset frequency parameter, the processor is further configured to adjust the light source to decrease the CCT of the light or decrease the bluish component of the light.

9. The illumination apparatus of claim 2, wherein the detector comprises at least two vertically arranged ultrasonic sensors and at least two horizontally arranged ultrasonic sensors.

10. A method of providing illumination, for reading or working, comprising the steps of:
   a) detecting postures of user within a time period and generating a plurality of signals corresponding to the time period;
   b) determining the status of the user within the time period, based on the plurality of signals; and
   c) generating light corresponding to the determined status of the user to adjust posture of the user or a concentration level of the user,
      wherein step b) comprises the steps of:
      i). determining a movement frequency, based on the plurality of signals;
      ii). comparing the determined movement frequency with a second preset frequency parameter so as to determine the status of the object;
      and step c) comprises the step of:
      iii). increasing the CCT of the light or increasing the bluish component of the light when the determined movement frequency is higher than the second preset frequency parameter.

11. The method of claim 10, wherein step a) comprises the steps of:
   i). measuring a first distance between a first part of the user and an illumination apparatus;
   ii). measuring a second distance between a second part of the user and the illumination apparatus;
   and the step b) comprises the steps of:
   iii). calculating an angle of bend, based on the first and the second distance;
   iv). comparing the angle of bend with a preset angle parameter to determine the status of the user;
   and the step c) comprises the step of:
   v). increasing at least one of the light intensity and the CCT of the light when the angle of bend is larger than the preset angle parameter.

12. The method of claim 10, wherein step b) comprises the steps of:
   i). determining a movement frequency, based on the plurality of signals;
   ii). comparing the determined movement frequency with a first preset frequency parameter so as to determine the status of the user;
   and step c) comprises the step of:
   iii). decreasing the CCT of the light or increasing the yellowish component of the light when the determined movement frequency is smaller than the first preset frequency parameter.

13. A computer readable, non-transitory medium having stored therein instructions for causing a processing unit to execute a method of providing illumination, the medium comprising the steps of:
   a) detecting postures of an object within a time period and generating a plurality of signals corresponding to the time period;
   b) determining the status of the object within the time period, based on the plurality of signals; and
   c) generating light corresponding to the determined status of the object;
      wherein step b) comprises the steps of:
      i). determining a movement frequency, based on the plurality of signals;
      ii). comparing the determined movement frequency with a second preset frequency parameter so as to determine the status of the object;
      and step c) comprises the step of:
      iii). increasing the CCT of the light or increasing the bluish component of the light when the determined movement frequency is higher than the second preset frequency parameter.

* * * * *